United States Patent [19]

Sircar et al.

[11] Patent Number: 4,820,697

[45] Date of Patent: Apr. 11, 1989

[54] 4,5-DIHYDRO-4,4-DIALKYL-6-(SUBSTITUTED)PHENYL-3(2H)-PYRIDAZINONES USEFUL AS CARDIOTONIC AGENTS

[75] Inventors: Ila Sircar; James A. Bristol; Richard W. Skeean, all of Ann Arbor, Mich.

[73] Assignee: Warner-Lambert Company, Morris Plains, N.J.

[21] Appl. No.: 928,434

[22] Filed: Nov. 10, 1986

Related U.S. Application Data

[63] Continuation of Ser. No. 685,640, Dec. 24, 1989, abandoned.

[51] Int. Cl.$^4$ ............... C07D 237/04; A61K 31/50
[52] U.S. Cl. .................... 514/252; 514/247; 544/238; 544/239
[58] Field of Search ............ 544/238, 239; 514/247, 514/252

[56] References Cited

U.S. PATENT DOCUMENTS

| | | | |
|---|---|---|---|
| 3,975,388 | 8/1976 | Hakim et al. | 544/239 |
| 4,353,905 | 10/1982 | Sircar et al. | 544/238 |
| 4,397,854 | 8/1983 | Sircar | 544/239 |
| 4,507,298 | 3/1985 | Lautenschlager et al. | 544/238 |
| 4,521,415 | 6/1985 | Katakami et al. | 544/238 |
| 4,599,332 | 7/1986 | Sircar | 544/238 |
| 4,717,730 | 1/1988 | Sircar | 544/238 |

FOREIGN PATENT DOCUMENTS

| | | |
|---|---|---|
| 0059688 | 9/1982 | European Pat. Off. . |
| 0075436 | 3/1983 | European Pat. Off. . |
| 0090978 | 10/1983 | European Pat. Off. . |
| 0117403 | 9/1984 | European Pat. Off. . |
| 2110329 | 6/1972 | France . |

OTHER PUBLICATIONS

Abstract from Derwent Publications, Ltd., 0059688, pp. 1802 to 1841.

*Primary Examiner*—Nicholas S. Rizzo
*Attorney, Agent, or Firm*—Joan Thierstein

[57] ABSTRACT

Novel 4,5-dihydro-4,4-dialkyl-6-(substituted)phenyl-3(2H)-pyridazinones having unexpected activity for use as cardiotonic and antihypertensive agents.

8 Claims, No Drawings

4,5-DIHYDRO-4,4-DIALKYL-6-(SUBSTITUTED)-PHENYL-3(2H)-PYRIDAZINONES USEFUL AS CARDIOTONIC AGENTS

This is a continuation of U.S. application Ser. No. 685,640 filed Dec. 24, 1984, now abandoned.

BACKGROUND OF THE INVENTION

Substituted 4,5-dihydro-6-(substituted)phenyl-3(2H)-pyridazinones and 6-(substituted)phenyl-3(2H)-pyridazinones useful as cardiotonic agents are the subject of U.S. Pat. No. 4,353,905 and U.S. application Ser. No. 477,695 filed Mar. 22, 1983 now 4,734,415. Additional references are cited therein to other known compounds.

SUMMARY OF THE INVENTION

The present invention relates to novel 4,5-dihydro-4,4-dialkyl-6-(substituted)phenyl-3(2H)-pyridazinone compounds having unexpectedly superior activity as cardiotonic agents of the formula

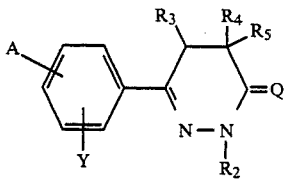
I wherein Q is oxygen or sulfur; $R_2$ and $R_3$ are independently hydrogen or lower alkyl; $R_4$ and $R_5$ are independently lower alkyl; Y is H, halogen, lower alkyl, lower alkoxy, or a group such as

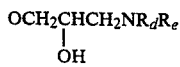

where $R_d$ and $R_e$ are independently H, lower alkyl, $(CH_2)_nR_f$ where $R_f$ is a benzene ring optionally substituted by halogen, hydroxy, lower alkyl, lower alkoxy, and $CF_3$, and n is zero to three, and A is any of the groups from a–e, and is attached to the 3- or 4-position of the phenyl ring:

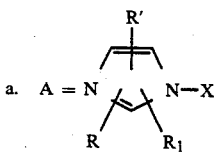

wherein $R_1$, R', and R are independently hydrogen or lower alkyl, $CH_2OH$, $SCH_3$, $SOCH_3$, $SO_2CH_3$, hydroxyalkyl, halogen, $(CH_2)_kNR''R'''$, wherein k is zero to two and R'' and R''' are independently hydrogen or lower alkyl, wherein lower alkyl contains one to six carbon atoms; or, when attached to the 4- and 5-positions of the imidazole ring, may be taken together to form a (i) 5-, 6-, or 7-membered ring which may also contain a nitrogen atom, (ii) benzene ring which is optionally substituted by halogen, hydroxy, lower alkyl, and lower alkyloxy, and (iii) pyridine ring; X is a bond, $(CH_2)_n$ or $O(CH_2)_n$ wherein n is one to four;

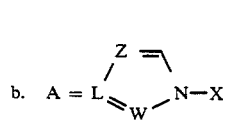

wherein
(i) W=L=Z=CH
(ii) W=Z=N and L=CH or
(iii) L=Z=N and W=CH; and X is a bond, $(CH_2)_n$ or $O(CH_2)_{n+1}$ wherein n is 1 to 4;

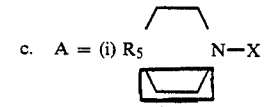

where $R_5$ is $CH_2$, O, S, $NR_6$ wherein $R_6$ is hydrogen, alkyl, $COR_7$ where $R_7$ is a benzene ring optionally substituted by halogen, lower alkyl, hydroxy, lower alkoxy, and $CF_3$ or $(CH_2)_nR_7$ where n is zero to four and $R_7$ is the same as defined above; or

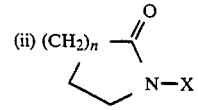

wherein n is one to three, or

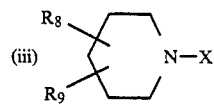

wherein $R_8$ and $R_9$ are independently hydrogen, lower alkyl, aryl, hydroxy, lower alkoxy, $NHR_{17}$ where $R_{17}$ is hydrogen, lower alkyl or lower alkanoyl, $CO_2R_{18}$ where $R_{18}$ is hydrogen or lower alkyl, $OCOBR_{10}$ where $R_{10}$ is alkyl, aryl or heteroaryl and B is a direct bond or NH, or $R_8$ and $R_9$ taken together, are carbonyl or ethylenedioxy;

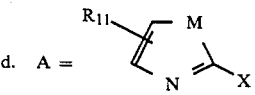

wherein ===== represents a double or single bond between two carbon atoms; $R_{11}$ is hydrogen or lower alkyl; M is NH, O, or S, and X is either a direct bond or NH; or

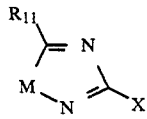

where X, M, and $R_{11}$ are the same as defined above; or
e. A=$NHPR_{12}R_{13}$ wherein P is a bond or carbonyl; $R_{12}$ is lower alkyl, straight or branched; $R_{13}$ is H, $NR_{14}R_{15}$ wherein $R_{14}$ and $R_{15}$ are individually hydrogen, lower alkyl straight or branched or taken together to form a 5-, or 6-, or 7-membered ring or a group as defined as 1a-1c: or $S(O)_nR_{16}$ where n is zero to two and $R_{16}$ is lower alkyl straight or branched, phenyl; and the pharmaceutically acceptable acid addition salts thereof.

Preferred compounds of formula I of the present invention are the compounds of formula I wherein Q is oxygen, Y is hydrogen, and A is

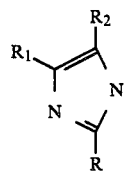

wherein R, $R_1$, and $R_2$ are independently H or lower alkyl, $R_1$ and $R_2$ may be taken together to form a (i) five or six membered ring and (ii) benzene ring; or A is $NHPR_{12}R_{13}$ wherein P is carbonyl, $R_{12}$ is lower alkyl, and $R_{13}$ is hydrogen and is attached to the four-position of the phenyl ring.

Most preferred compounds of the present invention are 4,5-dihydro-4,4-dimethyl-6-[4-(1H-imidazol-1-yl)phenyl]3(2H)pyridazinone and N-[4-(1,4,5,6-tetrahydro-5,5dimethyl-6-oxo-3-pyridazinyl)phenyl]-acetamide.

The present invention further relates to a cardiotonic composition for increasing cardiac contractility, said composition comprising an effective amount of a compound of formula I as defined above and a pharmaceutically acceptable carrier.

The present invention also relates to the method for increasing cardiac contractility in a patient requiring such treatment which comprises administering orally or parenterally in a solid or a liquid dosage form to such patient an effective amount of a compound of formula I as defined above.

The present invention relates to a pharmaceutical composition which also decreases blood pressure, said composition comprising an effective amount of a compound of formula I as defined above and a pharmaceutically acceptable carrier.

Finally, the present invention relates to the method of decreasing blood pressure in a patient requiring such treatment which comprises administering to such patient an effective amount of a compound of formula I as defined above.

DETAILED DESCRIPTION OF THE INVENTION

The detailed description of a cardiotonic composition and the pharmaceutical composition, which may be used for the compound of formula I above in combination with a pharmaceutically acceptable carrier, but not considering the unexpected activity of the present invention may be found in the above noted U.S. Pat. No. 4,353,905 and U.S. application Ser. No. 477,695 filed Mar. 22, 1983, which therefore, are hereby incorporated by reference. In the same manner the method of using the present compounds of formula I for increasing cardiac contractility and decreasing blood pressure can be ascertained from U.S. application Ser. No. 477,695 filed Mar. 22, 1983, when appropriately noting the unexpectedly relative activity of the present formula I compounds. The relative activity is as set out hereinafter.

The compounds of the present formula I are also useful in both the free base form and in the form of acid addition salts as described in U.S. application Ser. No. 477,695.

The terms "lower" in reference to alkyl and alkoxy, as well as "halogen" are as defined in U.S. application Ser. No. 477,695.

The relative activity showing unexpectedly superiority for the compounds of the present invention compared to those of the closest compounds of U.S. application Ser. No. 477,695 is shown in the following table.

TABLE

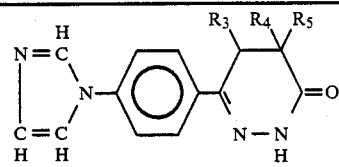

| | Compound | | | Dose | % Change | | |
| --- | --- | --- | --- | --- | --- | --- | --- |
| Ex. | $R_3$ | $R_4$ | $R_5$ | (mg/kg) | Myocardial Contractility | Heart Rate | Blood Pressure |
| | H | H | H | 0.01 | 9 | −4.0 | −2.0 |
| | | | | 0.03 | 32 | −4.0 | −6.0 |
| | | | | 0.10 | 57 | −1.0 | −10.5 |
| | | | | 0.31 | 87 | 2.0 | −21.5 |
| n = 1 | H | CH$_3$ | H | 0.01 | 0.5 | −1.0 | 0 |
| | | | | 0.03 | −2.0 | −4.5 | −1/−1 |
| | | | | 0.10 | 8.0 | −4.5 | 0/−1 |
| | | | | 0.31 | 26.5 | −1.5 | −5/−9.5 |
| | | | | 1.0 | 61.0 | 3.0 | −7/−14.5 |
| 1* | H | CH$_3$ | CH$_3$ | 0.01 | 15.0 | 1.5 | −1/−1.5 |
| n = 1 | | | | 0.03 | 34.0 | 4.0 | −6/−10 |
| | | | | 0.10 | 70.0 | 17.0 | −11/−16.5 |
| | | | | 0.31 | 101.5 | 21.5 | −22/−34 |
| | | | | 1.0 | 99.0 | 30.5 | −21.5/−31.5 |
| n = 5 | CH$_3$ | H | H | 0.01 | 50.6 ± 11.2 | 6.0 ± 5.3 | −1.7 ± 1.1 |
| n = 5 | | | | 0.03 | 124.0 ± 29.4 | 25.2 ± 8.2 | −7.4 ± 1.3 |
| n = 6 | | | | 0.10 | 148.5 ± 22.5 | 43.8 ± 12.0 | −19.0 ± 1.3 |
| n = 4 | | | | 0.31 | 118.5 ± 31.7 | 47.5 ± 15.5 | −35.2 ± 1.3 |
| n = 3 | | | | 1.0 | 58.6 ± 12.9 | 33.3 ± 13.3 | −45.0 ± 4.9 |
| n = 1 | CH$_3$CH$_3$ | H | H | 0.01 | 1 | 0 | 1/0 |
| | | | | 0.03 | 5 | 0 | −1/−2 |

TABLE-continued

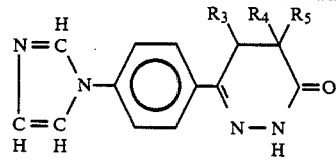

| Ex. | Compound | | | Dose (mg/kg) | % Change | | |
|---|---|---|---|---|---|---|---|
| | $R_3$ | $R_4$ | $R_5$ | | Myocardial Contractility | Heart Rate | Blood Pressure |
| | | | | 0.1 | 20 | 1 | −1/−2 |
| | | | | 0.31 | 73 | 5 | −8/−9 |
| | | | | 1.0 | 98 | 15 | −15/−17 | n = number of tests
*Compound of the present invention

The test procedure for methods of use of the present invention, are as described in U.S. application Ser. No. 477,695.

The following Example further illustrates the present invention without, however, limiting thereto.

EXAMPLE 1

4,5-Dihydro-4,4-dimethyl-6-[4-(1H-imidazol-1-yl)phenyl]-3(2H)-pyridazinone

Imidazole (0.70 g, 0.013 mol) and methyl α,α-dimethyl-4-fluoro-γ-oxobenzene butanoate (2.85 g, 0.012 mol) are dissolved in dimethyl sulfoxide (12.0 ml) in which freshly pulverized potassium carbonate (5.80 g, 0.042 mol) is suspended. The resulting mixture is stirred and heated at 100°–110° for 12 hours. The mixture is then cooled to room temperature and poured into 100 ml of ice water and stirred for ten minutes. The solid is filtered to give 2.14 g of methyl α,α-dimethyl-4-(1H-imidazol-1-yl)-γ-oxobenzene butanoate, mp 89°–93° C.

Methyl-α,α-dimethyl-4-(1H-imidazol-1-yl)γ-oxobenzene butanoate (1.8 g, 0.0066 mol) is dissolved in ethanol (25 ml) and 1.0 ml of 54% aqueous hydrazine is added. The resulting mixture is refluxed for ten hours, then another 0.5 ml aqueous hydrazine is added and the mixture is refluxed for an additional four hours.

The solution is evaporated to dryness and the residue is triturated with a small volume of ice-cold ethanol and collected on a suction funnel to give 1.2 g of the title compound, mp 199°–200° C.

Calcd. for $C_{15}H_{16}N_4O$; C, 67.14; H, 6.01; N, 20.89. C, 66.91; H, 5.88; N, 20.74.

We claim:

1. A compound of the formula:

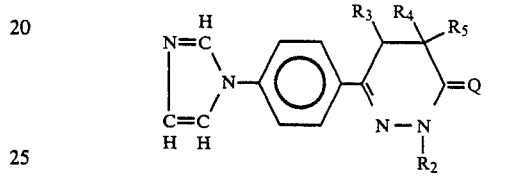

wherein Q is oxygen or sulfur; $R_2$ and $R_3$ are independently hydrogen or lower alkyl; $R_4$ and $R_5$ are independently lower alkyl.

2. A compound of claim 1 wherein Q is oxygen; Y is hydrogen, and A is

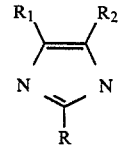

and is attached to four-position of the phenyl ring; wherein R, $R_1$, and $R_2$ are H or lower alkyl; $R_1$ and $R_2$ may be taken together to form a (i) five or six membered ring and (ii) benzene ring.

3. A compound of claim 1 wherein Q is oxygen, Y is hydrogen, and A is $NHPR_{12}R_{13}$ wherein P is carbonyl, $R_{12}$ is lower alkyl, and $R_{13}$ is hydrogen and is attached to the four-position of the phenyl ring.

4. A compound of claim 3 wherein the compound is N-[4-(1,4,5,6-tetrahydro-5,5-dimethyl-6-oxo-3-pyridazinyl)phenyl]-acetamide.

5. A compound of claim 2 wherein the specific embodiment is 4,5-dihydro-4,5-dimethyl-6-[4-1H-imidazol-1-yl)phenyl-3(2H)-pyridazinone.

6. A pharmaceutical composition for increasing cardiac contractility comprising an amount effective for increasing cardiac contractility or a compound as claimed in claim 1 with a pharmaceutically acceptable carrier.

7. The method for increasing cardiac contractility in a patient requiring such treatment comprising administering to such patients an effective amount of the composition of claim 6.

8. The method for lowering blood pressure in a patient suffering from hypertension comprising administering to such patients an effective amount of a composition of claim 6.

* * * * *